United States Patent [19]
Oda et al.

[11] 3,983,152
[45] Sept. 28, 1976

[54] 9-OXO-11α-HYDROXYMETHYL-15ξ-HYDROXYPROST-13(TRANS)-ENOIC ACID DERIVATIVES AND PROCESS FOR THE PREPARATION THEREOF

[75] Inventors: Osamu Oda; Kiyoshi Sakai; Takashi Yusa; Hamako Katano, all of Tokyo, Japan

[73] Assignee: Sankyo Company Limited, Tokyo, Japan

[22] Filed: Aug. 6, 1973

[21] Appl. No.: 385,868

[30] Foreign Application Priority Data
Sept. 1, 1972   Japan................................ 47-88172

[52] U.S. Cl........................... 260/468 D; 260/390.9;
260/343.3 R; 260/410.9 R; 260/413;
260/463; 260/488 R; 260/514 D; 424/305;
424/317
[51] Int. Cl.²...................................... C07C 177/00
[58] Field of Search................... 260/468 D, 514 D

[56] References Cited
UNITED STATES PATENTS
3,849,474   11/1974   Abraham et al.................... 260/468
FOREIGN PATENTS OR APPLICATIONS
2,313,868   10/1973   Germany........................... 260/468
OTHER PUBLICATIONS
Harrison et al., Tet. Letters, 5151 (1972).
Chemical Abstracts, 80, 59566v (1974).

*Primary Examiner*—Robert Gerstl
*Attorney, Agent, or Firm*—Flynn & Frishauf

[57] ABSTRACT
Prostanoic acid derivatives having the formula

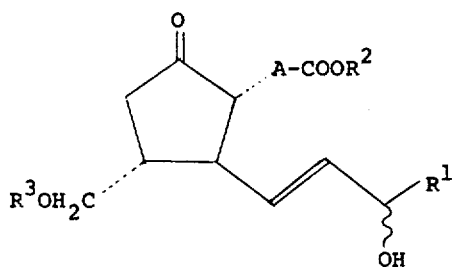

wherein A represents an alkylene group having from 4 to 8 carbon atoms, $R^1$ represents an alkyl group having from 4 to 10 carbon atoms, $R^2$ represents hydrogen atom or an alkyl group having from one to 6 carbon atoms and $R^3$ represents hydrogen atom or an alkoxycarbonyl group having from one to 6 carbon atoms in the alkyl moiety and the pharmaceutically acceptable salts thereof and also relates to a process for the preparation thereof.

The compounds are useful as oxytocic agents and may be prepared by reducing the compound having the formula

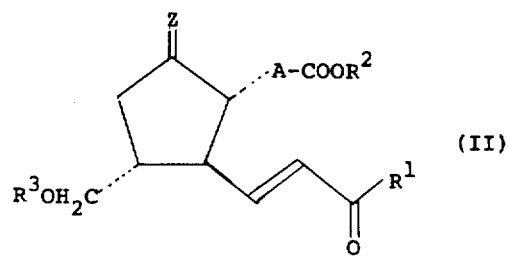

wherein A, $R^1$, $R^2$ and $R^3$ are the same as above and Z represents a carbonyl-protecting group with a metal hydride complex in the presence or absence of an inert organic solvent to give a compound having the formula

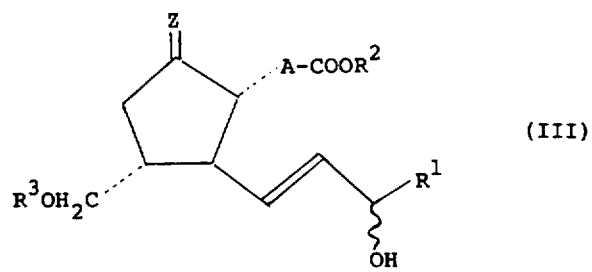

wherein A, $R^1$, $R^2$, $R^3$ and Z are the same as above and removing the carbonyl-protecting group of the latter compound.

6 Claims, No Drawings

9-OXO-11α-HYDROXYMETHYL-15ξ-HYDROXY-PROST-13(TRANS)-ENOIC ACID DERIVATIVES AND PROCESS FOR THE PREPARATION THEREOF

This invention relates to novel prostaglandin derivatives and a novel process for the preparation thereof.

More particularly, it relates to prostaglandin derivatives having the formula

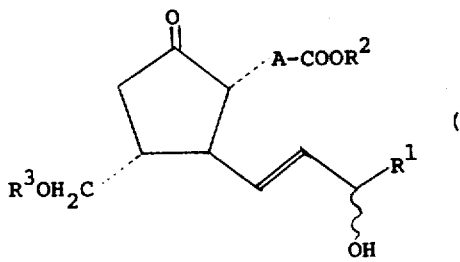

wherein A represents an alkylene group having from 4 to 8 carbon atoms, $R^1$ represents an alkyl group having from 4 to 10 carbon atoms, $R^2$ represents hydrogen atom or an alkyl group having from one to 6 carbon atoms and $R^3$ represents hydrogen atom or an alkoxycarbonyl group having from one to 6 carbon atoms in the alkyl moiety and the pharmaceutically acceptable salts thereof and also relates to a process for the preparation thereof.

In the above formula (I), A may be a straight or branched alkylene group having from 4 to 8 carbon atoms, preferably, pentamethylene, 1-methylpentamethylene, 2-methylpentamethylene, hexamethylene, 1-methylhexamethylene, 2-methylhexamethylene, heptamethylene, 1-methylheptamethylene and n-octamethylene. $R^1$ may be a straight or branched alkyl group having from 4 to 10 carbon atoms, preferably, n-butyl, isobutyl, n-pentyl, isopentyl, 1-methylpentyl, 2-methylpentyl, 1,1-dimethylpentyl, 1,2-di-methylpentyl, n-hexyl, isohexyl, 1-methylhexyl, 1,1-dimethylhexyl, 1,2-dimethylhexyl, n-heptyl and n-octyl. $R^3$ may be hydrogen atom or an alkoxycarbonyl group having from one to 6 carbon atoms, e.g., ethoxycarbonyl, n-propoxycarbonyl and n-butoxycarbonyl.

A preferred group of the prostaglandin derivatives provided by the invention are those of the formula (I) wherein A represents a hexamethylene group, i.e., those having the formula

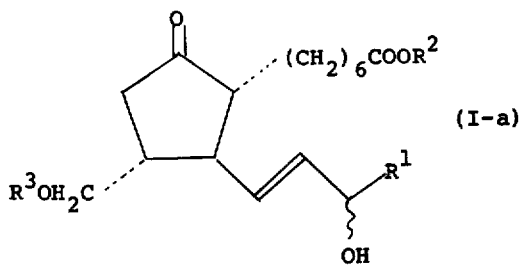

wherein $R^1$, $R^2$ and $R^3$ are the same as above and the pharmaceutically acceptable salts thereof.

In formulae (I) and (I-a), and elsewhere in this specification, a bond attached to the cyclopentane nucleus which is in the α-configuration, i.e., extends below the plane of the cyclopentane ring, is represented by a dotted line, and a bond which is in the β-configuration, i.e., extends above the plane of the cyclopentane ring, is represented by a solid line. The wavy line indicates that either steric configuration is possible.

The pharmaceutically acceptable salts of the acids of formulae (I) and (I-a) in which $R^2$ is hydrogen atom include alkali and alkaline earth metal salts, e.g., the sodium, potassium, magnesium and calcium salts, quaternary ammonium salts, e.g., the ammonium, tetramethylammonium, tetraethylammonium, benzyltrimethylammonium and phenyltriethylammonium salts, aliphatic, alicyclic or aromatic amine salts, e.g., the methylamine, ethylamine, dimethylamine, diethylamine, trimethylamine, triethylamine, N-methylhexylamine, cyclopentylamine, dicyclohexylamine, benzylamine, dibenzylamine, α-phenylethylamine and ethylenediamine salts, heterocyclic amine salts, e.g., the piperidine, morpholine, pyrrolidine, piperazine, pyridine, 1-methylpiperazine and 4-ethylmorpholine salts, salts of amines which are water-soluble or contain a hydrophilic group, e.g., the monoethanolamine, ethyldiethanolamine and 2-amino-1-butanol salts. Such salts may be prepared from the acids of formulae (I) and (I-a) in which $R^2$ is hydrogen atom by the conventional techniques.

The present prostaglandin derivatives exhibit a potent uterus-contracting activity and have no or little hypotensive and intestinal tube-contracting activity. For example, a full-term pregnant rat uterus is contracted intermittently for 15 minutes by intravenous injection of the following prostaglandin derivatives dissolved in isotonic sodium chloride solution containing a small amount of sodium bicarbonate.

| | |
|---|---|
| a racemic mixture of 9-oxo-11α-hydroxymethyl-15α-hydroxyprost-13(trans)-enoic acid | 60 – 70 μg/kg |
| a racemic mixture of 9-oxo-11α-hydroxymethyl-15α-hydroxy-16,16-dimethylprost-13(trans)-enoic acid | 5 μg/kg |
| $PGE_1$ | 35 μg/kg |

Uterus-contracting activity was measured by recording changes in intraamniotic pressure from a balloon introduced into the amniotic cavity through the cervix.

Accordingly, the compounds of the invention are useful as oxytocic agents; and the invention provides pharmaceutical compositions comprising a compound of formula (I), or a pharmaceutically acceptable salt thereof, and a pharmaceutical carrier or diluent. The pharmaceutical compositions of the invention are generally formulated for parenteral administration. For example, the compounds of formula (I) may be administered by continuous intravenous infusion, dissolved in sterile, pyrogen-free isotonic sodium chloride solution. The optimum dosage of the compounds of the invention will vary with the body weight and age of the patient; but the parenteral total daily dosage for full-term pregnant women will generally be from about 1 mg to 150 mg.

According to the present invention, the compound having the formula (I) may be prepared by reducing a compound having the formula

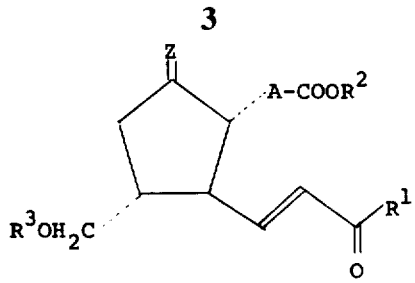

wherein A, R¹, R² and R³ are the same as above and Z represents a carbonyl-protecting group with a metal hydride complex in the presence or absence of an inert organic solvent to give a compound having the formula

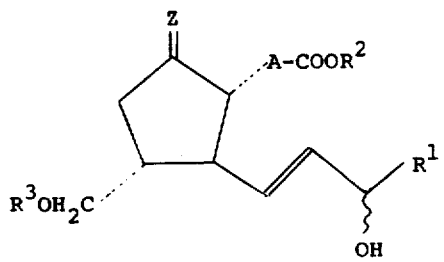

wherein A, R¹, R², R³ and Z are the same as above and removing the carbonyl-protecting group of the latter compound.

Preferable examples of the carbonyl-protecting group include an oxime group; a dialkoxy group, e.g., dimethoxy and diethoxy; and alkylenedioxy group, e.g., methylenedioxy and ethylene dioxy; and an alkylenedithio group, e.g., ethylenedithio and trimethylenedithio.

The reduction may be preferably carried out by contacting the compound (II) with the metal hydride complex in the presence of an inert organic solvent. Preferable examples of the metal hydride complex include alkali metal boron hydrides, e.g., sodium boron hydride, potassium boron hydride, lithium boron hydride, sodium cyano boron hydride, lithium 9b-boroperhydrophenalene hydride; alkali metal aluminum hydrides, e.g., aluminum tri-tert-butoxylithium hydride, aluminum trimethoxylithium hydride; and zinc boron hydride. Preferable examples of the inert organic solvent include alcohols, e.g., methanol and ethanol; ethers, e.g., diethyl ether, tetrahydrofuran, dioxane, diglyme; and dialkylformamides, e.g., dimethylformamide. The reduction is preferably carried out at relatively low temperatures, usually at a temperature from −10°C to room temperature. The reaction period will depend mainly upon the reaction temperature and a kind of the reducing agent. It is usually from about 30 minutes to 3 hours.

After completion of the reaction, the desired product may be recovered from the reaction mixture by conventional means. For instance, organic acids, e.g., formic acid and acetic acid, are added to the reaction mixture in order to decompose the excess reducing agent and the mixture is extracted with an organic solvent. The extract is washed with water and dried and the solvent is distilled off to give the desired product.

The product thus obtained may be further purified, if necessary, by conventional means, for example, column chromatography or thin-layer chromatography. The reaction for eliminating the carbonyl-protecting group may vary depending on the kind of the protecting group used. In cases where the protecting group is, for example, oxime, it may be removed by being contacted with an acid. The acid used is preferably mineral acids, such as, for example, hydrochloric acid, sulfuric acid and nitrous acid and organic acids, such as, for example, pyruvic acid. In cases where the protecting group is, for example, dialkoxy group, such as, for example, dimethoxy and diethoxy, alkylenedioxy group, such as, for example, methylenedioxy and ethylenedioxy, it may be removed by being contacted with an acid. The acid used is preferably an organic acid, such as, for example, formic acid, acetic acid, propionic acid, butyric acid, oxalic acid, malonic acid, p-toluenesulfonic acid and picric acid, and mineral acids, such as, for example, hydrochloric acid, hydrobromic acid and sulfuric acid. In cases where the protecting group is, for example, an alkylenedithio group, such as ethylenedithio and trimethylenedithio, it may be removed by being contacted with mercuric chloride. The reaction may be preferably carried out in the presence of solvent. The solvent used is not limited so far as the solvent is inert to the present reaction, and is preferably water; alcohols, such as methanol and ethanol; ethers, such as tetrahydrofuran and dioxane; ketone, such as acetone; or mixed solvents of the said organic solvent with water. The reaction temperature is not limited, but is preferably at temperatures from room temperature to about 60°C. The reaction time may vary mainly depending on the kind of a protecting group to be removed and the conditions of removing reaction employed.

After completion of the reaction, the object compound (II) may be recovered from the reaction mixture by means of a common method. For example, it is obtained by, after the reaction, neutralizing the reaction mixture by adding a base such as sodium acetate thereto, evaporating the solvent from the reaction mixture, extracting the resulting residue by adding an organic solvent thereto, washing the extract with water followed by drying, and evaporating the solvent from the extract. The object compound thus obtained may be further purified, if necessary, by means of a usual method, such as, for example, column chromatography and thin-layer chromatography.

The compounds of the formula (I) and their salts can exist as four different optical isomers, depending upon the configuration of the hydroxyl groups attached to the cyclopentane nucleus and the side-chain. The racemic mixtures of these isomers can be resolved by the conventional techniques, so as to obtain the desired products in the form of optically pure diastereoisomers. The formulae (I) and (I-a) are used to represent both diastereoisomeric forms, as well as the racemic mixtures, but the pure isomers are included within the scope of the invention, as well as their mixtures. The group R² and R³ may be removed by conventional means, for example, by treating with an acid, e.g., acetic acid, hydrochloric acid or with a base, e.g., sodium hydroxide, sodium carbonate.

The compound of the formula (II), employed as a starting material in the preparation of the compound of the invention, is also novel and can be prepared by the process shown in the following reaction schemes.

PREPARATION OF THE COMPOUNDS (II)
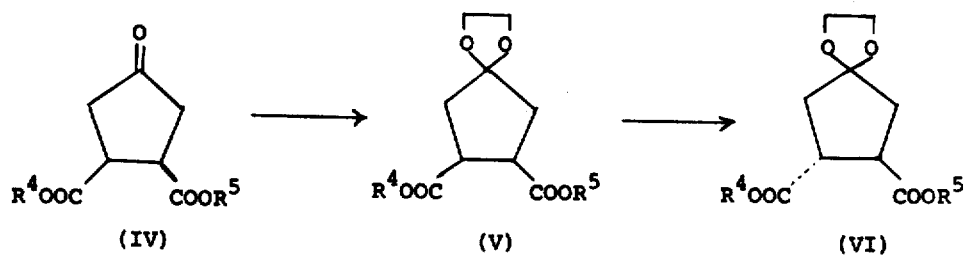
J. Org. Chem., 36, 1277 (1971)
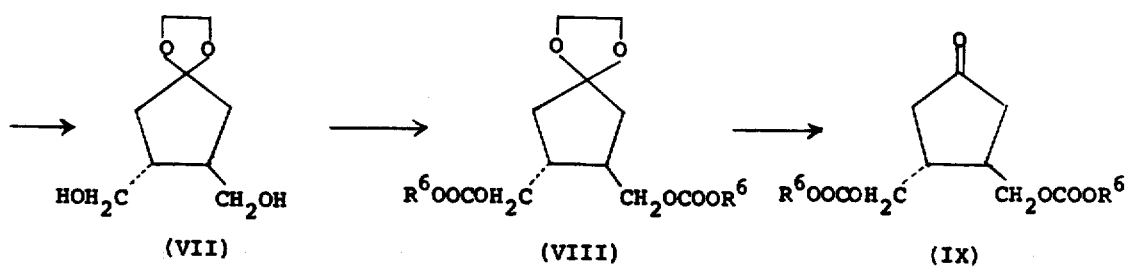
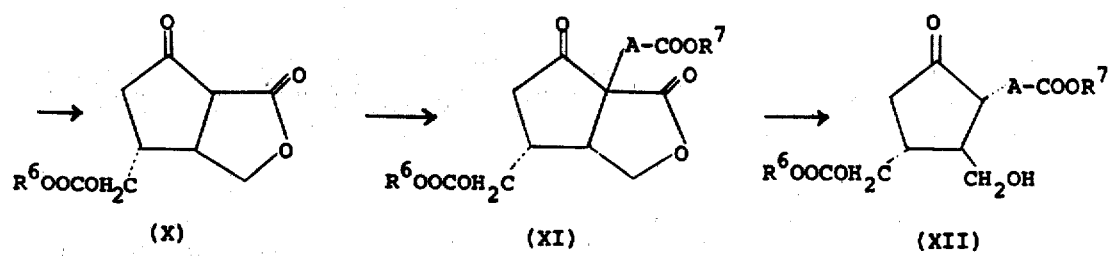
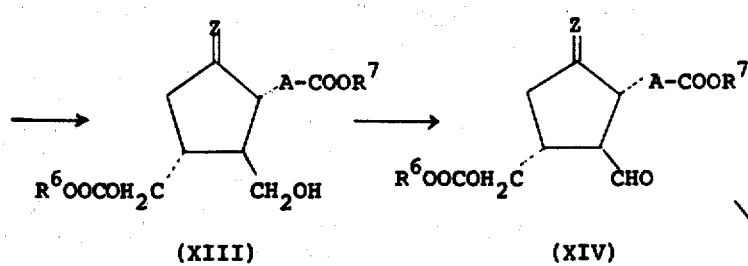
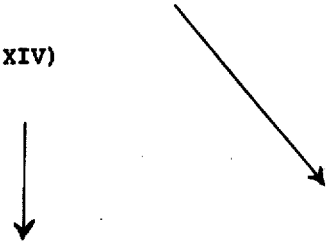

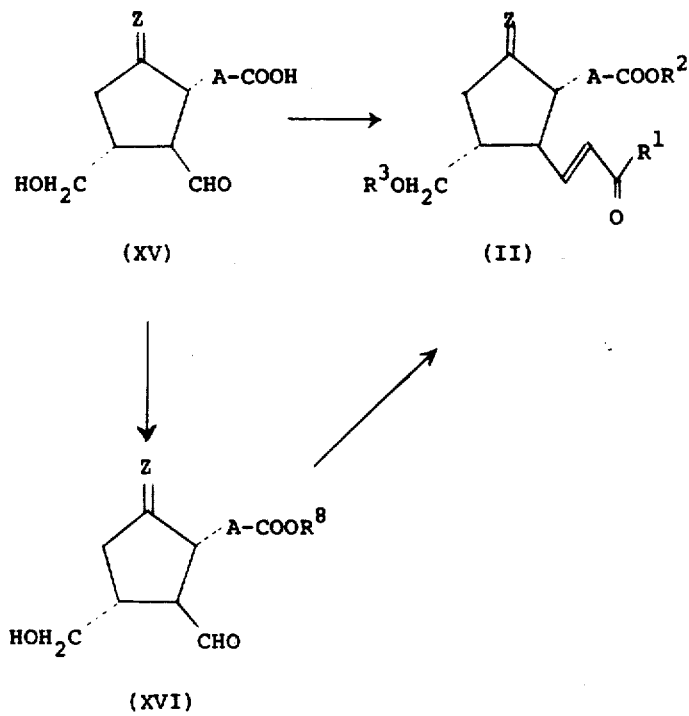

In the above scheme, A, $R^1$, $R^2$, $R^3$ and Z are the same as above and $R^4$, $R^5$, $R^6$, $R^7$ and $R^8$ may be the same or different and each represents an alkyl group having 1 – 6 carbon atoms.

Each of the above steps may be illustrated as follows;

The compound (V) may be prepared by reacting the compound (IV) with ethylene glycol in the presence of a Lewis acid, e.g., boron trifluoride.

The reaction is preferably carried out in an inert organic solvent such as dichloromethane, chloroform or benzene at temperatures from 0°C to room temperature.

The compound (VI) may be prepared by reacting the compound (V) with an alkali metal compound, e.g., sodium methoxide, potassium ethoxide, sodium hydroxide. The reaction is preferably carried out in an inert organic solvent such as tetrahydrofuran, dioxane or methanol at temperatures from 0°C to a reflux temperature of the reaction mixture.

The compound (VII) may be prepared by reducing the compound (VI) with a metal hydride compound such as sodium boron hydride, potassium boron hydride, lithium boron hydride, trimethoxylithium aluminum hydride and aluminum lithium hydride. The reaction is preferably carried out in an inert organic solvent such as methanol, tetrahydrofuran or ether at temperatures from 0°C to a reflux temperature of the reaction mixture.

The compound (VIII) may be prepared by reacting the compound (VII) with a compound having the formula $X^1$-COOR$^6$ wherein $R^6$ is the same as above and $X^1$ represents a halogen atom, e.g., chlorine, bromine, iodine in the presence of a base such as sodium carbonate, sodium bicarbonate, triethylamine, pyridine or N-methylpiperizine. The reaction is preferably carried out below room temperature.

The compound (IX) may be prepared by reacting the compound (VIII) with an acid such as formic acid, acetic acid, hydrochloric acid, hydrobromic acid or sulfuric acid. The reaction is preferably carried out in a solvent such as water, methanol, ether or acetone at temperatures from 0°C to 60°C.

The compounds (X) may be prepared by reacting the compound (IX) with a base such as alkali metal alkoxides, e.g., sodium methoxide, potassium ethoxide, potassium tert-butoxide; alkali metal hydrides, e.g., sodium hydride, potassium hydride; or alkali metal hydroxides, e.g., sodium hydroxide, potassium hydroxide. The reaction is preferably carried out in an inert organic solvent such as tetrahydrofuran, ether and benzene at temperatures from −50°C to 80°C in an inert gas, e.g., argon, helium.

The compound (XI) may be prepared by reacting the compound (X) with a compound having the formula $X^2$-A-COOR$^7$ wherein A and $R^7$ are the same as above and $X^2$ represents a halogen atom, e.g., iodine, bromine, chlorine, in the presence of a base such as alkali metals, e.g., metallic sodium; alkali metal hydroxides, e.g., sodium hydroxide, potassium hydroxide; or alkali metal alkoxides, e.g., sodium methoxide, potassium ethoxide. The reaction is preferably carried out in an inert organic solvent, e.g., benzene, ether, tetrahydrofuran, hexamethyl phosphoramide, dimethyl sulfoxide, below room temperature in an inert gas, e.g., argon, helium.

The compound (XII) may be prepared by reacting the compound (XI) with a base such as sodium hydroxide, ammonium acetate, sodium phosphate-dibasic, potassium hydroxide, sodium carbonate or potassium carbonate. The reaction is preferably carried out in a solvent, e.g., water, methanol, ether, dioxane, a mixture of water and such an organic solvent, at temperatures from room temperature to reflux temperature of the reaction mixture in an inert gas, e.g., argon, helium.

The compound (XIII) may be prepared by contacting the compound (XII) with a compound capable of forming a carbonyl-protecting group. Preferable examples of the compound which can form a carbonyl-protecting group include hydroxylamines such as hydroxylamine or methylhydroxylamine sodium hydroxylaminesulfonate which form an oxime group; orthoformic acid esters such as methyl orthoformate, ethyl orthoformate, which form a ketal group; alkylene glycols such as methylene glycol or ethylene glycol, which form a ring ketal group; and alkylene dithioglycol such as ethylene dithioglycol or trimethylene dithioglycol, which form a thioketal ring.

The reaction of the compound (XII) with the hydroxylamines is carried out in the presence of a base, e.g., sodium hydroxide. The reaction of the compound (XII) with orthoformic acid esters, alkylene glycols or alkylene dithioglycols is carried out in the presence of a small amount of an acid, for example, mineral acids such as hydrochloric acid or sulfonic acid, organic acids such as benzenesulfonic acid, p-toluenesulfonic acid, picric acid or trifluoroacetic acid and Lewis acids such as boron trifluoride, aluminum chloride or zinc chloride. When orthoformic acid esters are used as a reagent, there may be preferably employed concentrated sulfonic acid or hydrogen chloride. When alkylene glycols are used as a reagent, there may be preferably employed p-toluenesulfonic acid. The reaction may be preferably carried out in the presence of a solvent such as benzene, toluene, dichloromethane or chloroform. The reaction is usually carried out at reaction temperatures from room temperature to a reflux temperature of the reaction mixture. When the mineral acids or Lewis acids are used, the reaction is preferably carried out at −20°C to room temperature. When organic acids are used, the reaction is preferably carried out at an approximate reflux temperature of the solvent used.

The compound (XIV) may be prepared by contacting the compound (XIII) with an oxidizing agent such as chromic acid, chromic anhydride, chromic anhydride-pyridine complex, sodium bichromate, dimethyl sulfoxide-chlorine complex, methyl sulfide-N-chlorosuccinimide. The reaction is preferably carried out in a solvent such as acetic acid, dichloromethane, chloroform at temperatures from 0°C to room temperature.

The compound (XV) may be prepared by contacting the compound (XIV) with an acid such as formic acid, acetic acid, hydrochloric acid or sulfuric acid, or with a base such as sodium hydroxide, potassium hydroxide or sodium carbonate. The reaction is preferably carried out in a solvent, e.g., water, methanol, ether, at temperatures from room temperature to reflux temperature of the reaction mixture.

The compound (XVI) may be prepared by subjecting the compound (XV) to esterification with an alcohol, e.g., methanol and ethanol or a diazoalkane, e.g., diazomethane and diazoethane.

The compound (II) may be prepared by reacting the compound (XIV), (XV) or (XVI) with a Wittig reagent having the formula

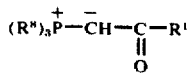

wherein $R^1$ is the same as above and $R^x$ represents an alkyl group having 2 – 5 carbon atoms or a phenyl group. At least one mole of the Wittig reagent is used per mole of the compound (XIV), (XV) or (XVI) and preferably from 2 to 10 moles of the Wittig agent is used.

The reaction is generally carried out in an inert organic solvent such as ether, benzene, toluene, hexane, dimethyl sulfoxide, tetrahydrofuran, methylene chloride or chloroform, at temperatures of from 0°C to a reflux temperature of the reaction mixture, preferably at room temperature or below and in an inert gas, e.g., argon, helium. The reaction is carried out for a period of 5 hours to 30 hours depending on the temperature and concentration of the reaction mixture and the specific Wittig reagent used.

The product obtained in each step of the above process may be recovered from the reaction mixture in a conventional manner, for example, by evaporating the solvent from the reaction mixture or by adding water and extracting with a water-immiscible solvent. The crude product can be purified by conventional means such as recrystallization or chromatography.

The following preparations and examples are given for the purpose of illustration of the present invention.

PREPARATION 1

Preparation of 9-ethylenedioxy-11α-hydroxymethyl-15-oxoprost-13(trans)-enoic acid (II)

1. 1-Ethylenedioxy-3,4-dimethoxycarbonylcyclopentane (V)

In 250 ml of dichloromethane were dissolved 124 g of 3,4-dimethoxycarbonylcyclopentanone and 155 g of ethylene glycol and to the solution was added dropwise 94 g of boron trifluoride ethyl etherate at 0° – 5°C. After completion of the addition, the reaction mixture was stirred for 2 hours at 10° – 16°C and next for 1.5 hours at 16° – 23°C. After completion of the reaction, the reaction mixture was added dropwise to 1.5l of a saturated aqueous sodium bicarbonate containing pieces of ice in order to decompose the excess of the boron trifluoride etherate. The mixture was extracted three times with 1 l of ether. The extract was washed with a saturated aqueous sodium chloride and a saturated aqueous sodium bicarbonate and dried over anhydrous sodium sulfate. The solvent was distilled off from the extract to give 135.7 g of the desired product as colorless oil.

I.R. (liquid film) $\nu_{max}$cm$^{-1}$:
1741, 1438, 1329, 1200, 1030

N.M.R. (CDCl$_3$) δ : ppm
3.63, 3.69 (6H, each singlet, cis and trans —COO$\underline{C}$H$_3$)
3.90 (4H, singlet,

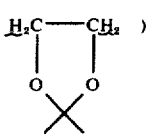

2. 1-Ethylenedioxy-trans-3,4-dimethoxycarbonylcyclopentane (VI)

In 3200 ml of dry benzene was dissolved 178 g of 1-ethylenedioxy-3,4-dimethoxycarbonylcyclopentane and to the solution was added dropwise a sodium methoxide solution prepared from 16.8 g of metallic sodium and 730 ml of absolute methanol in argon atmosphere at 0° – 5°C. After completion of the addition, the solution was stirred for 2 hours at 5°C and next for 3 hours at 20° – 22°C. After completion of the reaction, the reaction mixture was cooled to 0°C and added to about 2.2 l of ice-water containing 80 ml of acetic acid under stirring. The reaction mixture was saturated with sodium chloride and the benzene layer was separated. The aqueous layer was extracted with 2 l of ether and 1 l of ethyl acetate. The extracts were combined, washed with a saturated aqueous sodium chloride and dried over anhydrous sodium sulfate. The solvent was distilled off from the extract under reduced pressure to give 173 g of pale yellow oil. The oil was subjected to vacuum distillation to give 155.8 g of the pure desired product as oil boiling at 120° – 123°C under 0.05 mm pressure of mercury.

I.R. (liquid film) $\nu_{max}$cm$^{-1}$:
1741, 1438, 1329, 1200, 1030
N.M.R. (CCl$_4$) δ : ppm
3.63 (6H, singlet, trans-COOC$\underline{H}_3$)
3.83 (4H, singlet,

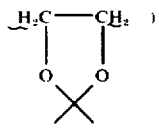
)

3. 1-Ethylenedioxy-trans-3,4-dihydroxymethylcyclopentane (VII)

In 400 ml of dry ether was dissolved 78 g of 1-ethylenedioxy-trans-3,4-dimethoxycarbonylcyclopentane and the resulting solution was added dropwise to a suspension of 30.3 g of lithium aluminum hydride in 300 ml of dry ether at 5°C. After completion of the addition, the mixture was stirred for 3 hours. After completion of the reaction, 500 ml of ether saturated with water and 130 ml of a saturated aqueous sodium chloride were added to the reaction mixture below 10°C to decompose the excess lithium aluminum hydride. The ether was separated from the reaction mixture by decantation. The aqueous layer was extracted with ether and further subjected to evaporation under reduced pressure.

The residue was extracted with absolute ethanol. All of the extract were combined and dried over anhydrous sodium sulfate. The solvent was distilled off to give 68.4 g of the desired product as pale yellow oil.

I.R. (liquid film) $\nu_{max}$cm$^{-1}$:
3400, 2900, 1433, 1141, 1013, 950
N.M.R. (CCl$_4$) δ : ppm
3.15 – 3.78 (4H, multiplet, -C$\underline{H}_2$OH)
3.80 (4H, singlet,

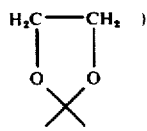
)

4.50 (2H, singlet, -OH)
4. 1-Ethylenedioxy-trans-3,4-diethoxycarbonyloxymethylcyclopentane (VIII)

In 1 l of dry pyridine was dissolved 113 g of 1-ethylenedioxy-1-trans-3,4-dihydroxymethylcyclopentane and to the solution was added dropwise 250 g of ethyl chloroformate (ClCOOC$_2$H$_5$) below 5°C.

After completion of the addition, the reaction mixture was stirred for 30 minutes at that temperature and next for 2 hours at room temperature. After completion of the reaction, the reaction mixture was added to 2 l of ice water and the mixture was extracted with ether. The extract was washed with a saturated aqueous sodium chloride and dried over anhydrous sodium sulfate. The solvent was distilled off to give 188.2 g of the desired product as pale yellow oil.

I.R. (liquid film) $\nu_{max}$cm$^{-1}$:
1750, 1469, 1403, 1372, 1260, 1010, 949, 875, 791
N.M.R. (CDCl$_3$) δ : ppm
1.15 – 1.50 (6H, triplet, -OCH$_2$C$\underline{H}_3$)
3.88 (4H, singlet,

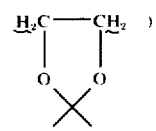
)

4.00 – 4.35 (8H, multiplet, -C$\underline{H}_2$OCOOC$\underline{H}_2$CH$_3$)
5. Trans-3,4-diethoxycarbonyloxymethylcyclopentane-1-one (IX)

In a mixture of 800 ml of acetone, 20 ml of water and 2.5 ml of 10% hydrochloric acid was dissolved 56.5 g of 1-ethylenedioxy-trans-3,4-diethoxycarbonyloxymethylcyclopentane and the solution was stirred for one hour at room temperature and further for 2 hours at 50°C after addition of 2.0 g of p-toluenesulfonic acid.

After completion of the reaction, the reaction mixture was added to 2 l of ice-water and saturated with sodium chloride. The mixture was extracted with benzene. The extract was washed with saturated aqueous sodium chloride and dried over anhydrous sodium sulfate. The solvent was distilled off to give 51.0 g of the desired product as pale yellow oil. The oil was subjected to column chromatography using 250 g of silica gel washed with hydrochloric acid and eluted some amounts of n-hexane and next successively n-hexane-benzene (1:1) - benzene-ethyl acetate (95:5). The solvent was distilled off from the elution to give 47.3 g of the desired product as oil.

I.R. (liquid film) $\nu_{max}$cm$^{-1}$:
1748, 1469, 1408, 1376, 1260, 1009, 877, 792
N.M.R. (CDCl$_3$) δ : ppm
1.18 – 1.50 (6H, triplet, -OCH$_2$C$\underline{H}_3$)
4.30 (4H, singlet, -C$\underline{H}_2$OCOOCH$_2$CH$_3$)
4.02 – 4.41 (4H, quartette, -CH$_2$OCOOC$\underline{H}_2$CH$_3$)
6. 2-Carboxy-3-hydroxymethyl-4α-ethoxycarbonyloxymethylcyclopentane-1-one-2,3(γ)-lactone (X)

In 700 ml of dry tetrahydrofuran was dissolved 28.83 g of trans-3,4-diethoxycarbonyloxymethylcyclopentane-1-one and to the solution was added dropwise a solution of 16.9 g of potassium tert-butoxide in 900 ml of dry tetrahydrofuran in an argon atmosphere at −45°C. After completion of the addition, the reaction temperature was slowly elevated to 10°C. The completion of the reaction was confirmed with chromatography.

The reaction mixture was again cooled to −20°C and added to about 2 l of ice water containing 50 ml of acetic acid under vigorous agitation. To the mixture was added sodium chloride and the mixture was extracted with ether and benzene.

The extract was washed with a saturated aqueous sodium chloride and dried over anhydrous sodium sulfate. The solvent was distilled off to give 27.0 g of pale yellow oil. To the oil was added ether-n-hexane and the mixture was allowed to cool to give 10.5 g of the desired product as crystals. The mother liquor was subjected to column chromatography using silica gel and eluted with benzene to give 4.1 g of crystals. The total yield was 14.6 g. Melting point was 65° − 66°C.

I.R. (Nujol) $\nu_{max}$cm$^{-1}$:
1772, 1747, 1290, 1283, 1258, 1168, 1150, 1029 880, 790
N.M.R. (CDCl$_3$) δ : ppm
1.20 − 1.46 (3H, triplet, —OCH$_2$C$\underline{H}_3$)
3.00 − 3.45 (1H, multiplet,

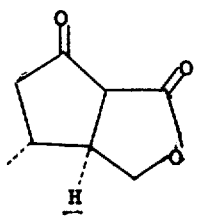

3.46 − 3.58 (1H, doublet,

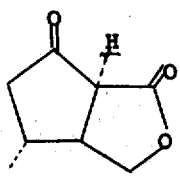

4.10 − 4.73 (6H, multiplet,

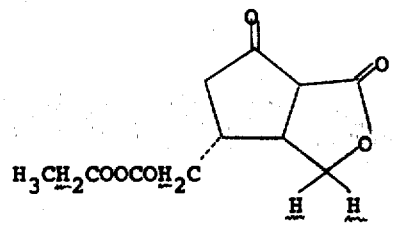

Analysis: Calculated for C$_{11}$H$_{14}$O$_6$; C, 54.54; H, 5.83. Found; C, 54.88 H, 6.07.

7. 2-(6-Methoxycarbonylhexyl)-2-carboxy-3-hydroxymethyl-4α-ethoxycarbonyloxymethylcyclopentane-1-one-2,3(γ)-lactone (XI)

In 60 ml of dimethyl sulfoxide was dissolved 6.54 g of 2-carboxy-3-hydroxymethyl-4-ethoxycarbonyloxymethylcyclopentane-1-one-2,3(γ)-lactone and to the solution was added 4.85 g of potassium tert-butoxide in argon atmosphere under cooling and the mixture was stirred for 60 minutes at room temperature. To the mixture was added 10.9 g of methyl 7-iodoenanthate and the mixture was stirred for 6 hours at room temperature. After completion of the reaction, the reaction mixture was added to 500 ml of ice water containing 27 ml of acetic acid and the mixture was extracted with ethyl acetate and benzene. The extract was washed with a saturated aqueous sodium chloride and dried over anhydrous sodium sulfate. The solvent was distilled off to give 15 g of the pale yellow oil. The oil was subjected to column chromatography using 120 g of silica gel and eluted with some amounts of n-hexane and next successively with n-hexane-benzene (1:4). The eluates with n-hexane-benzene were collected and the solvent was distilled off to give 6.2 g of the desired product as oil.

I.R. (liquid film $\nu_{max}$cm$^{-1}$:
2940, 1785, 1744, 1462, 1438, 1408, 1372, 1260, 1169, 1094, 1030, 1009, 872, 791
N.M.R. (CDCl$_3$) δ : ppm
1.20 − 1.45 (3H, triplet, —OCH$_2$C$\underline{H}_3$)
2.60 − 3.10 (1H, multiplet,

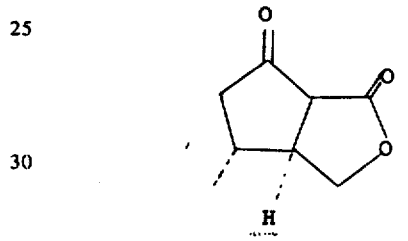

3.63 (3H, singlet, -COOC$\underline{H}_3$)
4.05 − 4.6 (6H, multiplet,

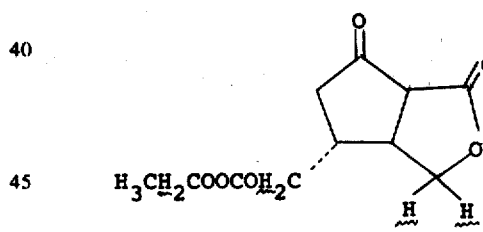

8. 2α-(6-Methoxycarbonylhexyl)-3β-hydroxymethyl-4α-ethoxycarbonyloxymethylcyclopentane-1-one (XII)

In a solution of 90 ml of dioxane, 24 ml of water and 2.43 g of potassium carbonate was dissolved 6.12 g of 2-(6-methoxycarbonylhexyl)-2-carboxy-3-hydroxymethyl-4-ethoxycarbonyloxymethylcyclopentane-1-one-2,3(γ)-lactone and the resulting solution was stirred in argon atmosphere for 3 days at room temperature. After completion of the reaction, the reaction mixture was added to 500 ml of ice water containing 10 ml of acetic acid.

The mixture was extracted with ethyl acetate. The extract was washed with a saturated aqueous sodium chloride and dried over anhydrous sodium sulfate. The solvent was distilled off to give 6.1 g of pale yellow oil. The oil was subjected to column chromatography using 48 g of silica gel and eluted with some amounts of n-hexane and next successively with n-hexane-benzene (1:2) - benzene-ethyl acetate (99:1). The eluates with n-hexane-benzene (1:2) - benzene-ethyl acetate (99:1) were collected and the solvent was distilled off to give 4.50 g of the desired product as oil.

I.R. (liquid film) $v_{max}$cm$^{-1}$:
3540, 2940, 1742, 1440, 1370, 1258, 1172, 1008, 873, 792
N.M.R. (CDCl$_3$) δ : ppm
0.90 - 1.34 (3H, triplet, -OCH$_2$C$\underline{H}_3$)
3.44 (3H, singlet, -COOC$\underline{H}_3$)
3.50 - 4.20 (6H, multiplet, -C$\underline{H}_2$OH and -C$\underline{H}_2$O-COOCH$_2$CH$_3$)
5.30 (1H, singlet, -CH$_2$O$\underline{H}$)

9. 1-Ethylenedioxy-2α-(6-methoxycarbonylhexyl)-3β-hydroxymethyl-4α-ethoxycarbonyloxymethylcyclopentane (XIII)

To a mixture of 2.02 g of 2α-(6-methoxycarbonylhexyl)-3β-hydroxymethyl-4α-ethoxycarbonyloxymethylcyclopentane-1-one, 3.5 g of ethylene glycol and 6 ml of dichloromethane was added dropwise 3.0 g of boron trifluoride diethyl etherate under ice cooling. After completion of the addition, the reaction mixture was stirred for 2 hours at −10°C - −15°C and next for 3 hours at 0°C. After completion of the reaction, the reaction mixture was poured into a saturated aqueous sodium bicarbonate containing pieces ice and the mixture was saturated with sodium chloride. The mixture was extracted with ether and the extract was dried over anhydrous sodium sulfate. The solvent was distilled off to give 2.3 g of pale yellow oils. The oils were subjected to column chromatography using 12.5 g of silica gel and eluted with some amounts of n-hexane and next successively with n-hexane-benzene (2:1 - 1:1). The eluates with n-hexane-benzene (2:1 - 1:1) were collected and the solvent was distilled off to give 1.25 g of the desired product as oil.

I.R. (liquid film) $v_{max}$cm$^{-1}$:
3520, 2930, 1788, 1740, 1440, 1370, 1255, 1100, 1010, 951, 874, 791
N.M.R. (CDCl$_3$) δ : ppm
3.70 (3H, singlet, -COOCH$_3$)
3.91 (4H, singlet,

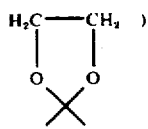

4.00 - 4.50 (6H, multiplet, -CH$_2$OH and -CH$_2$O-COOCH$_2$CH$_3$)

10. 1-Ethylenedioxy-2α-(6-carboxyhexyl)-3β-formyl-4α-hydroxymethylcyclopentane (IX)

In 60 ml of dichloromethane was dissolved 1.04 g of 1-ethylenedioxy-2α-(6-methoxycarbonylhexyl)-3β-hydroxymethyl-4α-ethoxycarbonyloxymethylcyclopentane and to the solution was added 6.7 g of chromic anhydride-pyridine complex (Collins reagent). The mixture was stirred for 10 minutes at room temperature. After completion of the reaction, 100 ml of ether was added to the reaction mixture and the mixture was stirred for a while and filtered with Hyflo Super Cel (trade name of Johns Manville Sales Corp.). The precipitate was washed with ether and the washing was combined with the filtrate. The organic layer was washed successively with a cooled 2% aqueous sodium hydroxide, a cooled 2% aqueous hydrochloric acid, a cooled 5% aqueous sodium bicarbonate and a saturated aqueous sodium chloride respectively, and dried over anhydrous sodium sulfate. The solvent was distilled off from the organic layer to give 935 mg of the desired product as pale yellow oils.

I.R. (liquid film) $v_{max}$cm$^{-1}$:
2940, 1784, 1740, 1440, 1370, 1255, 1165, 1100, 1015, 951, 875, 791
N.M.R. (CDCl$_3$) δ : ppm
3.68 (3H, singlet, -COOC$\underline{H}_3$)
3.92 (4H, singlet,

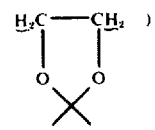

4.00 - 4.50 (4H, multiplet, -C$\underline{H}_2$OCOOC$\underline{H}_2$CH$_3$)
9.60 - 9.90 (1H, multiplet, -C$\underline{H}$O)

11. 1-Ethylenedioxy-2α-(6-carboxyhexyl)-3β-formyl-4α-hydroxymethylcyclopentane (XV)

In a mixture of 70 ml of methanol, 13 ml of water and 7 ml of a 10% aqueous potassium hydroxide was dissolved 1.60 g of 1-ethylenedioxy-2α-(6-methoxycarbonylhexyl)-3β-formyl-4α-ethoxycarbonyloxymethylcyclopentane and the solution was stirred for 4 hours at room temperature in an argon atmosphere. After completion of the reaction, the reaction mixture was added to ice water containing 4 ml of acetic acid with vigorous stirring. The mixture was extracted with ethyl acetate. The extract was washed with a small amount of an aqueous sodium chloride and dried over anhydrous sodium sulfate. The solvent was distilled off from the extract to give 860 mg of the desired product as pale yellow oils.

I.R. (liquid film) $v_{max}$cm$^{-1}$:
3450, 2710, 1720

12. 9Ethylenedioxy-11α-hydroxymethyl-15-oxo-prost-13(trans)-enoic acid (II)

In 30 ml of ether was dissolved 620 mg of 1-ethylenedioxy-2α-(6-carboxyhexyl)-3β-formyl-4α-hydroxymethylcyclopentane and to the solution was added 760 mg of 2-oxoheptylidenephosphorane. The mixture was stirred for 13 hours at room temperature in an argon atmosphere. After completion of the reaction, the solvent was distilled off from the reaction mixture under reduced pressure to give 1.49 g of yellowish orange oils. The oils were subjected to column chromatography using 12 g of silica gel and eluted with some amounts of benzene and next successively with benzene-ethyl acetate (99:1 - 98:2). The eluates with benzene-ethyl acetate (99:1 - 98:2) were collected and the solvent was distilled off to give 705 mg of the desired product as oils.

I.R. (liquid film) $v_{max}$cm$^{-1}$:
3450, 1710, 1678, 1631
N.M.R. (CDCl$_3$) δ : ppm

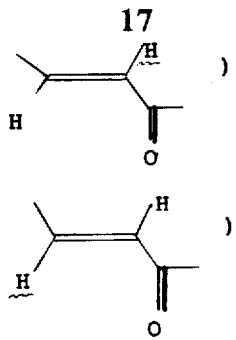

6.07 – 6.33 (1H, quartette,
6.56 – 6.93 (1H, quartette,

Preparation 2

Preparation of methyl 9-ethylenedioxy-11α-ethoxycarbonyloxymethyl-15-oxoprost-13(trans)-enoate (II)

In 40 ml of ether was dissolved 910 mg of 1-ethylenedioxy-2α-(6-methoxycarbonylhexyl)-3β-formyl-4α-ethoxycarbonyloxymethylcyclopentane and to the solution was added 932 mg of 2-oxoheptylidene-tri-n-butylphosphorane. The mixture was stirred for 16 hours at room temperature in an argon atmosphere. After completion of the reaction, the solvent was distilled off from the reaction mixture under reduced pressure to give 1.9 g of yellowish orange oils. The oils were subjected to column chromatography using 18.5 g of silica gel and eluted with some amounts of n-hexane and next with n-hexane-benzene (2:1). The eluates with the latter solvent were collected and the solvent was distilled to give 1.07 g of the desired product as oils.

I.R. (liquid film) $\nu_{max}$cm$^{-1}$:
2940, 1746, 1677, 1630, 1460, 1370, 1257, 1170 1100, 1010, 950, 872, 791
N.M.R. (CDCl$_3$) δ : ppm
0.70 – 1.05 (3H, triplet, —CH$_2$C$\underline{H}_3$)
3.68 (3H, singlet, —COOC$\underline{H}_3$)
3.91 (4H, singlet,

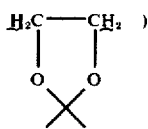

3.78 – 4.40 (4H, multiplet, -CH$_2$OCOOCH$_2$CH$_3$)
5.96 – 6.22 (1H, doublet,

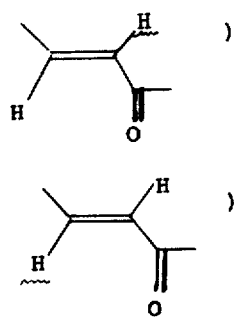

6.52 – 6.95 (1H, quartette,

Preparation 3

Preparation of methyl 9-ethylenedioxy-11α-ethoxycarbonyloxymethyl-15-oxo-16,16-dimethylprost-13(trans)-enoate (II)

In 40 ml of anhydrous tetrahydrofuran was dissolved 2.5 g of 1-ethylenedioxy-2α-(6-methoxycarbonylhexyl)-3β-formyl-4α-ethoxycarbonyloxymethylcyclopentane and to the solution was added 2.8 g of 2-oxo-3,3-dimethylheptylidene-tri-n-butylphosphoran. The mixture was heated under reflux in an argon atmosphere for 70 hours. After completion of the reaction, the solvent was distilled off and the residue was subjected to column chromatography using 60 g of silica gel and eluted with a 5 – 10% ethyl acetate solution in benzene to give 2.0 g of the desired product.

I.R. (liquid film) $\nu_{max}$cm$^{-1}$:
1740, 1695, 1625
N.M.R. (CDCl$_3$) δ : ppm
1.05 (3H, singlet, —C$\underline{H}_3$)
1.10 (3H, singlet, —C$\underline{H}_3$)
3.70 (3H, singlet, —C$\underline{H}_3$)

EXAMPLE 1

9-Oxo-11α-hydroxymethyl-15α(and β)-hydroxyprost-13(trans)-enoic acid [a]

1. 9-Ethylenedioxy-11α-hydroxymethyl-15ξ-hydroxyprost-13(trans)-enoic acid

To a solution of 615 mg of 9-ethylenedioxy-11α-hydroxymethyl-15-oxoprost-13(trans)-enoic acid in 25 ml of ethanol was added a solution of 230 mg of sodium boron hydride in 13 ml of ethanol under ice cooling and the mixture was stirred for 2 hours at 0° – 5°C. After completion of the reaction, the reaction mixture was added to about 100 ml of ice-water and the pH of the mixture was adjusted to 4.0 by addition of acetic acid. The mixture was extracted with ethyl acetate and the extract was dried over anhydrous sodium sulfate. The solvent was distilled off from the extract to give 603 mg of the desired product as pale yellow oils.

I.R. (liquid film) $\nu_{max}$cm$^{-1}$:
3450, 2940, 1717, 1460, 1260, 1154, 1030, 972 951
N.M.R. (CDCl$_3$) δ : ppm
0.60 – 1.10 (3H, triplet, -CH$_2$C$\underline{H}_3$)
3.94 (4H, singlet,

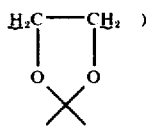

3.30 – 4.30 (3H, multiplet)
5.40 – 5.74 (2H, multiplet,

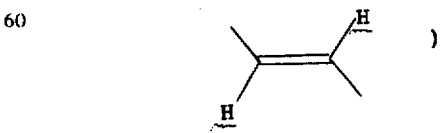

5.90 (3H, singlet, -O$\underline{H}$ and -COO$\underline{H}$)
2. 9-Oxo-11α-hydroxymethyl-15α(and β)-hydroxyprost-13(trans)-enoic acid In a solution of 12 ml of acetone, 2.5 ml of water and 10 mg of p-toluenesulfonic acid was dissolved 596 mg of 9-ethylenedioxy-11α-hydroxymethyl-15ε-hydroxyprost-13(trans)-enoic acid and the solution was stirred for one hour at room temperature. After completion of the reaction, the reaction mixture was dried over anhydrous sodium sulfate and the solvent was distilled off. To the residues was added about 25 ml of ice water and the mixture was saturated with sodium chloride. The mixture was extracted with ethyl acetate. The extract was washed with a saturated aqueous sodium chloride and dried over anhydrous sodium sulfate. The solvent was distilled off to give 563 mg of pale yellow oils. The oils were subjected to column chromatography using 5.6 g of silica gel and eluted with some amounts of benzene and next with benzene-ethyl acetate (5:1). The eluates with the latter solvent were collected and the solvent was distilled off to give 163 mg of 9-oxo-11α-hydroxymethyl-15β-hydroxyprost-13(trans)-enoic acid. From the eluates with benzene-ethyl acetate (3:2) was obtained 150 mg of a mixture of 9-oxo-11α-hydroxymethyl-15β-hydroxyprost-13(trans)-enoic acid and 9-oxo-11α-hydroxymethyl-15α-hydroxyprost-13(trans)-enoic acid. Subsequently, from the eluates with benzene-ethyl acetate (1:1) was obtained 108 mg of 9-oxo-11α-hydroxymethyl-15α-hydroxyprost-13(trans)-enoic acid melting a 65°–57°C. The infrared absorption spectra and nuclear magnetic resonance spectra of the products thus obtained are all identical.

I.R. (liquid film) $\nu_{max}$cm$^{-1}$:
3400, 2940, 1730, 1460, 1405, 1260, 1163, 1052 1018, 972, 726

N.M.R. (CD$_3$COCD$_3$) δ : ppm
0.70 – 1.10 (3H, triplet, -CH$_2$C$\underline{H}_3$)
3.20 – 4.30 (6H, multiplet, -COO$\underline{H}$, >C$\underline{H}$OH, -C$\underline{H}_2$OH)
5.54 – 5.75 (2H, multiplet,

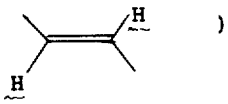
)

9-Oxo-11α-hydroxymethyl-15α-hydroxyprost-13(trans)-enoic acid was obtained as semicrystall by cooling. [b]

1. Methyl 9-ethylenedioxy-11α-ethoxycarbonyloxymethyl-15ξ-hydroxyprost-13(trans)-enoate To a solution of 920 mg of methyl 9-ethylenedioxy-11α-ethoxycarbonyloxymethyl-15-oxoprost-13(trans)-enoate in 40 ml of ethanol was added a solution of 280 mg of sodium boron hydride in 10 ml of ethanol under ice cooling and the mixture was stirred for 1 hour at 0° – 5°C. After completion of the reaction, the reaction mixture was added to about 100 ml of a cooled saturated aqueous sodium chloride. The mixture was extracted with ethyl acetate.

The extract was dried over anhydrous sodium sulfate and the solvent was distilled off to give 940 mg of pale yellow oils. The oils were subjected to column chromatography using 6 g of silica gel and eluted with some amounts of n-hexane and next with n-hexane-benzene (9:1). The eluates with the latter solvent were collected and the solvent was distilled off to give 720 mg of the desired product.

I.R. (liquid film) $\nu_{max}$cm$^{-1}$:
3500, 2940, 1746, 1462, 1440, 1371, 1260, 1011, 972, 949, 872, 792

N.M.R. (CDCl$_3$) δ : ppm
0.68 – 1.10 (3H, triplet, -CH$_2$C$\underline{H}_3$)
3.68 (3H, singlet, -COOC$\underline{H}_3$)
3.90 (4H, singlet,

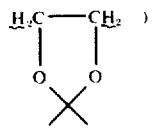
)

3.80 – 4.40 (5H, multiplet)
5.40 – 5.74 (2H, multiplet,

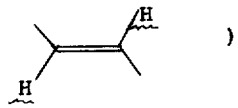
)

2. 9Oxo-11α-hydroxymethyl-15α(and β)-hydroxyprost-13(trans)-enoic acid

In a solution of 20 ml of methanol, 4 ml of water and 2 ml of 10% aqueous potassium hydroxide was dissolved 602 mg of methyl 9-ethylenedioxy-11α-ethoxycarbonyloxymethyl-15ξ-hydroxyprost-13(trans)-enoate and the solution was stirred for 6 hours in argon atmosphere at room temperature. After completion of the reaction, the reaction mixture was poured into about 100 ml of ice-water containing 1 ml of acetic acid and the mixture was extracted with ethyl acetate. The extract was dried over anhydrous sodium sulfate and the solvent was distilled off to give 540 mg of 9-ethylenedioxy-11α-hydroxymethyl-15-hydroxyprost-13(trans)-enoic acid as yellow oil.

The infrared absorption spectrum and nuclear magnetic resonance spectrum of the products thus obtained were the same as those of the products obtained in the above []-(1).

3. 9-Oxo-11α-hydroxymethyl-15α(and β)-hydroxyprost-13(trans)-enoic acid

In a solution of 10 ml of acetone, 0.2 ml of water and 10 mg of p-toluenesulfonic acid was dissolved 540 mg of 9-ethylenedioxy-11α-hydroxymethyl-15ξ-hydroxyprost-13(trans)-enoic acid and the solution was stirred for 1 hour at room temperature. After completion of the reaction, 5 mg of anhydrous sodium acetate was added to the reaction mixture and the mixture was stirred for 30 minutes. The solvent was distilled off from the reaction mixture. To the residue was added about 20 ml of ice water followed by saturation with sodium chloride. The mixture was extracted with ethyl acetate. The extract was washed with a saturated aqueous sodium chloride and dried over anhydrous sodium sulfate. The solvent was distilled off to give 520 mg of pale yellow oils. The oils were subjected to column chromatography using 5.0 g of silica gel and eluted with some amounts of benzene and next with benzene-ethyl acetate (5:1). The eluates with the latter solvent were collected and the solvent was distilled off to give 127 mg of 9-oxo-11α-hydroxymethyl-15β-hydroxyprost-13(trans)-enoic acid. From the eluates with benzene-ethyl acetate (3:2) was obtained 133 mg of a mixture of 9-oxo-11α-hydroxymethyl-15β-hydroxyprost-13(trans)-enoic acid and 9-oxo-11α-hydroxymethyl-15α-hydroxyprost-13(trans)-enoic acid. Subsequently, from the eluates with benzene-ethyl acetate (1:1) was obtained 71 mg of 9oxo-11α-hydroxymethyl-15α-hydroxyprost-13(trans)-enoic acid.

The infrared absorption spetra, nuclear magnetic resonance spectra and melting points of the products thus obtained were the same as those of the products obtained in the above [a].

EXAMPLE 2

Potassium 9-oxo-11α-hydroxymethyl-15α-hydroxyprost-13(trans)-enoate

In a mixture of 3 ml of methanol and 3 ml of water was dissolved 124 mg of 9-oxo-11α-hydroxymethyl-15α-hydroxyprost-13(trans)-enoic acid and to the solution was added 23.3 mg of potassium carbonate. The solution was stirred for 1 hour at room temperature and the solvent was distilled off under reduced pressure to give 137 mg of the desired product.

I.R. (liquid film) $\nu_{max}$cm$^{-1}$:
3400, 1730, 1580 – 1560

EXAMPLE 3

9-Oxo-11α-hydroxymethyl-15α(and β)-hydroxy-16,16-dimethylprost-13(trans)-enoic acid 1. Methyl 9-ethylenedioxy-11α-ethoxycarbonyloxymethyl-15ξ-hydroxy-16,16-dimethyprost-13(trans)-enoate To a solution of 1.91 g of methyl 9-ethylenedioxy-11α-ethoxycarbonyloxymethyl-15-oxo-16,16-dimethyprost-13(trans)-enoate in 60 ml of methanol was added 240 mg of sodium boron hydride under ice cooling and the mixture was stirred for 2 hours at room temperature. After completion of the reaction, the reaction mixture was made acidic by addition of acetic acid. The mixture was extracted three times with ethyl acetate. The extract was dried over anhydrous sodium sulfate and the solvent was distilled off. The residue was subjected to column chromatography using 20 g of silica gel and eluted with a 15 – 20% ethyl acetate solution in benzene to give 1.8 g of the desired product.

I.R. (liquid film) $\nu_{max}$cm$^{-1}$:
3500, 1740, 1260
N.M.R. (CDCl$_3$) δ : ppm
0.90 (3H, singlet, -CH$_3$)
0.82 (3H, singlet, -CH$_3$)

2. 9-Ethylenedioxy-11α-hydroxymethyl-15ξ-hydroxy-16,16-dimethylprost-13(trans)-enoic acid To a solution of 40 ml of 5% aqueous sodium hydroxide and 60 ml of methanol was added 1.68 g of methyl 9-ethylenedioxy-11α-ethoxycarbonyloxymethyl-15ξ-hydroxy-16,16-dimethylprost-13(trans)-enoate. The solution was stirred for 2 hours at room temperature, made acidic by addition of acetic acid and extracted with ethyl acetate. The solvent was distilled off to give 1.4 g of the desired product.

3. 9-Oxo-11α-hydroxymethyl-15α(and β)-hydroxy-16,16-dimethylprost-13(trans)-enoic acid In a mixture of 15 ml of acetic acid and 15 ml of water was dissolved 1.33 g of 9-ethylenedioxy-11α-hydroxymethyl-15ξ-hydroxy-16,16-dimethyprost-13(trans)-enoic acid and the solution was stirred for 2 hours at room temperature. The reaction mixture was extracted with ethyl acetate and dried over anhydrous sodium sulfate. The solvent was distilled off and the residue was subjected to column chromatography using 20 g of silica gel and eluted with 40 – 60% ethyl acetate in benzene to give at first 500 mg of 9-oxo-11α-hydroxymethyl-15α-hydroxy-16,16-dimethyprost-13(trans)-enoic acid and next 600 mg of 9-oxo-11α-hydroxymethyl-15β-hydroxy-16,16-dimethylprost-13(trans)-enoic acid.

the 15α-hydroxy compound;
I.R. (liquid film) $\nu_{max}$cm$^{-1}$:
3450, 1740
N.M.R. (CD$_3$COCD$_3$) δ : ppm
5.7 (2H, broad)
0.91 (3H, singlet, -CH$_3$)
0.88 (3H, singlet, -CH$_3$)
the 15β-hydroxy compound;
I.R. (liquid film) $\nu_{max}$cm$^{-1}$:
3450, 1740
N.M.R. (CD$_3$COCD$_3$) δ : ppm
5.7 (2H, broad)
0.91 (3H, singlet, -CH$_3$)
0.88 (3H, singlet, -CH$_3$)

What is claimed is:

1. Compounds having the formula

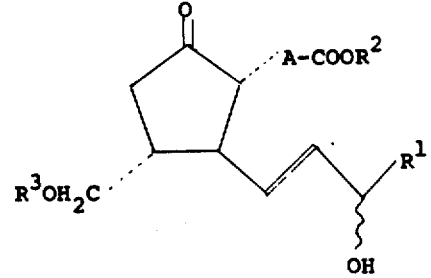

wherein A represents an alkylene group having from 4 to 8 carbon atoms, R$^1$ represents an alkyl group having fron 4 to 10 carbon atoms, R$^2$ represents hydrogen atom or an alkyl group having from one to 6 carbon atoms and R$^3$ represents hydrogen atom or an alkoxycarbonyl group having from one to 6 carbon atoms in the alkyl moiety and pharmaceutically acceptable salts thereof.

2. Compounds having the formula

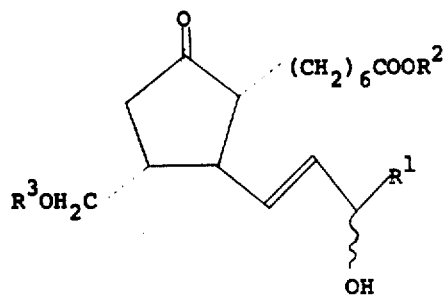

wherein R¹ represents an alkyl group having from 4 to 10 carbon atoms, R² represents hydrogen atom or an alkyl group having from one to 6 carbon atoms and R³ represents hydrogen atom or an alkoxycarbonyl group having from one to 6 carbon atoms in the alkyl moiety and pharmaceutically acceptable salts thereof.

3. 9-Oxo-11α-hydroxymethyl-15α(or β)-hydroxyprost-13(trans)-enoic acid.

4. Methyl 9-oxo-11α-hydroxymethyl-15α(or β)-hydroxyprost-13(trans(-enoate.

5. Potassium 9oxo-11α-hydroxymethyl-15α(or β)-hydroxyprost-13(trans)-enoate.

6. 9-Oxo-11α-hydroxymethyl-15α(or β)-hydroxy-16,16-dimethylprost-13(trans)-enoic acid.

* * * * *